United States Patent [19]

Budd

[11] Patent Number: 5,461,934
[45] Date of Patent: Oct. 31, 1995

[54] AMBIENT AIR COLLECTION DEVICE FOR USE WITH A SELF-CONTAINED BREATHING APPARATUS

[76] Inventor: Alexander G. Budd, 9 Carman Blvd., Brookhaven, N.Y. 11719

[21] Appl. No.: 359,440

[22] Filed: Dec. 20, 1994

[51] Int. Cl.⁶ .............................. G01N 1/14; A62B 9/02
[52] U.S. Cl. ................... 73/864.52; 128/204.22; 128/205.24; 128/201.28; 128/202.13; 128/204.18
[58] Field of Search ................ 128/201.25, 201.28, 128/201.22, 202.13, 204.18, 205.12, 205.27, 205.28, 205.29, 207.12, 204.22, 205.24; 95/8; 55/270; 73/864.52, 864.63

[56] References Cited

U.S. PATENT DOCUMENTS

| | | | |
|---|---|---|---|
| 4,195,524 | 4/1980 | Hansen | 73/864.52 |
| 4,476,708 | 10/1984 | Baker et al. | 73/23 |
| 4,949,582 | 8/1990 | Vollweiler | 73/864.63 X |
| 5,072,737 | 12/1991 | Goulding | 128/718 |
| 5,335,653 | 8/1994 | Blomqvist et al. | 128/204.18 |
| 5,368,021 | 11/1994 | Beard et al. | 128/205.12 |

FOREIGN PATENT DOCUMENTS

| | | | |
|---|---|---|---|
| 2557716 | 6/1977 | Germany | 73/864.52 |
| 4023839 | 2/1992 | Germany | 73/864.52 |

*Primary Examiner*—Kimberly L. Asher
*Assistant Examiner*—Eric P. Raciti

[57] ABSTRACT

An ambient air collection device comprising a primary induction valve having a body, an air inlet, an air outlet, an ambient air output port, a channel extended between the air inlet and air outlet, an actuation chamber having an input port coupled to the channel and an output port coupled to the ambient air output port, an ambient air intake valve coupled to the actuation chamber for delivering ambient air thereto, switch means positioned within the input port and output port of the actuation chamber and having a biased orientation for allowing transfer of ambient air within the actuation chamber to the ambient air output port based upon detection of a flow of breathable air through the channel and an unbiased orientation for preventing such transfer when no flow is detected; and a removable hollow vacuum pressurized vacuum test cylinder coupled to the ambient air output port for collecting the ambient air.

5 Claims, 4 Drawing Sheets

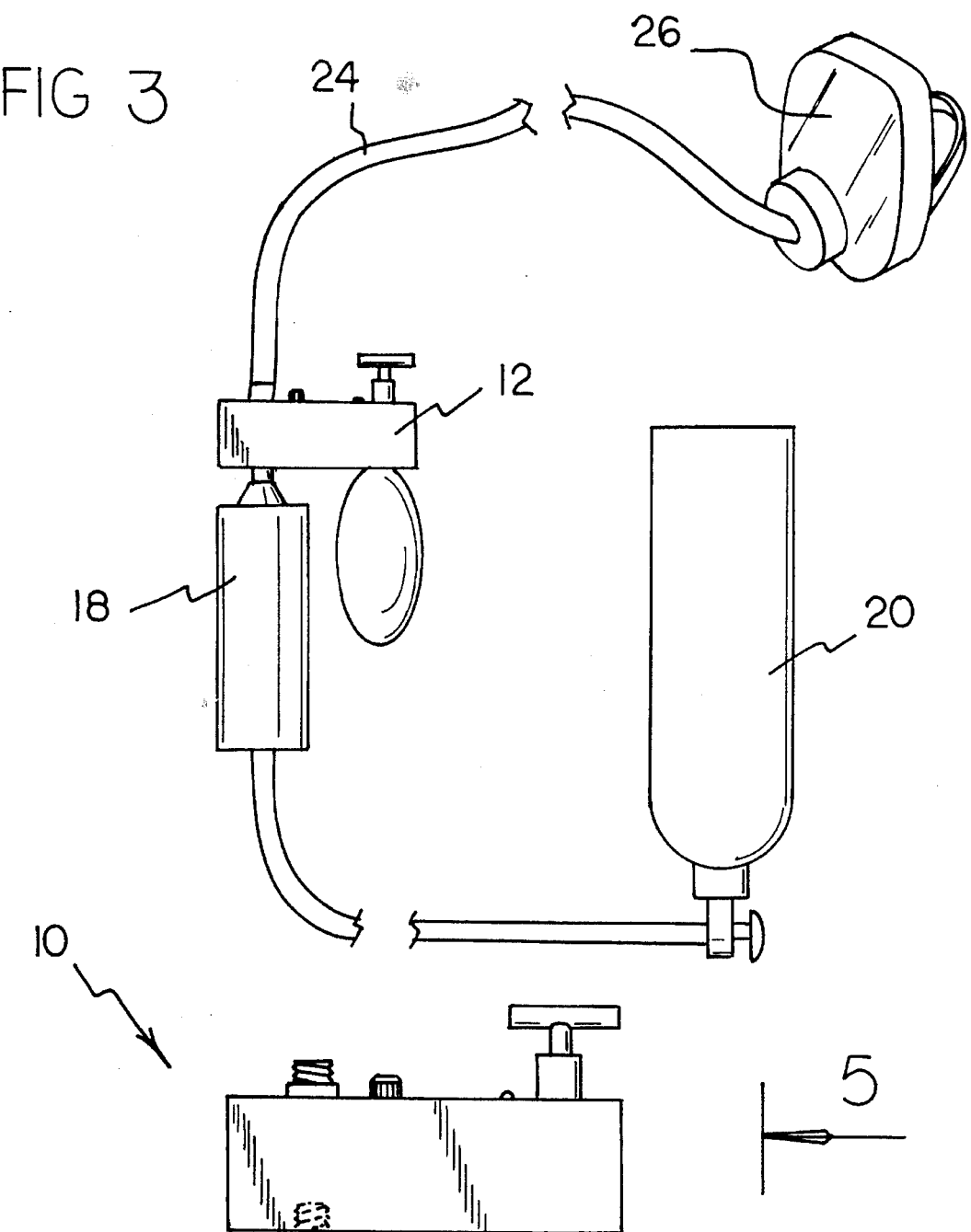
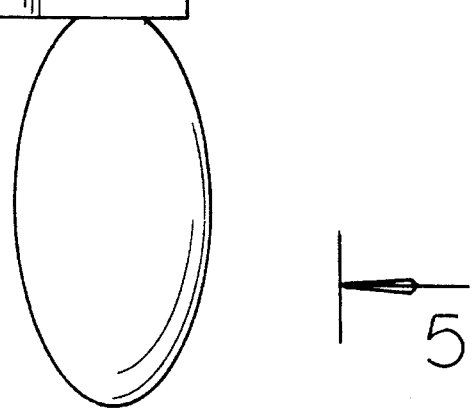

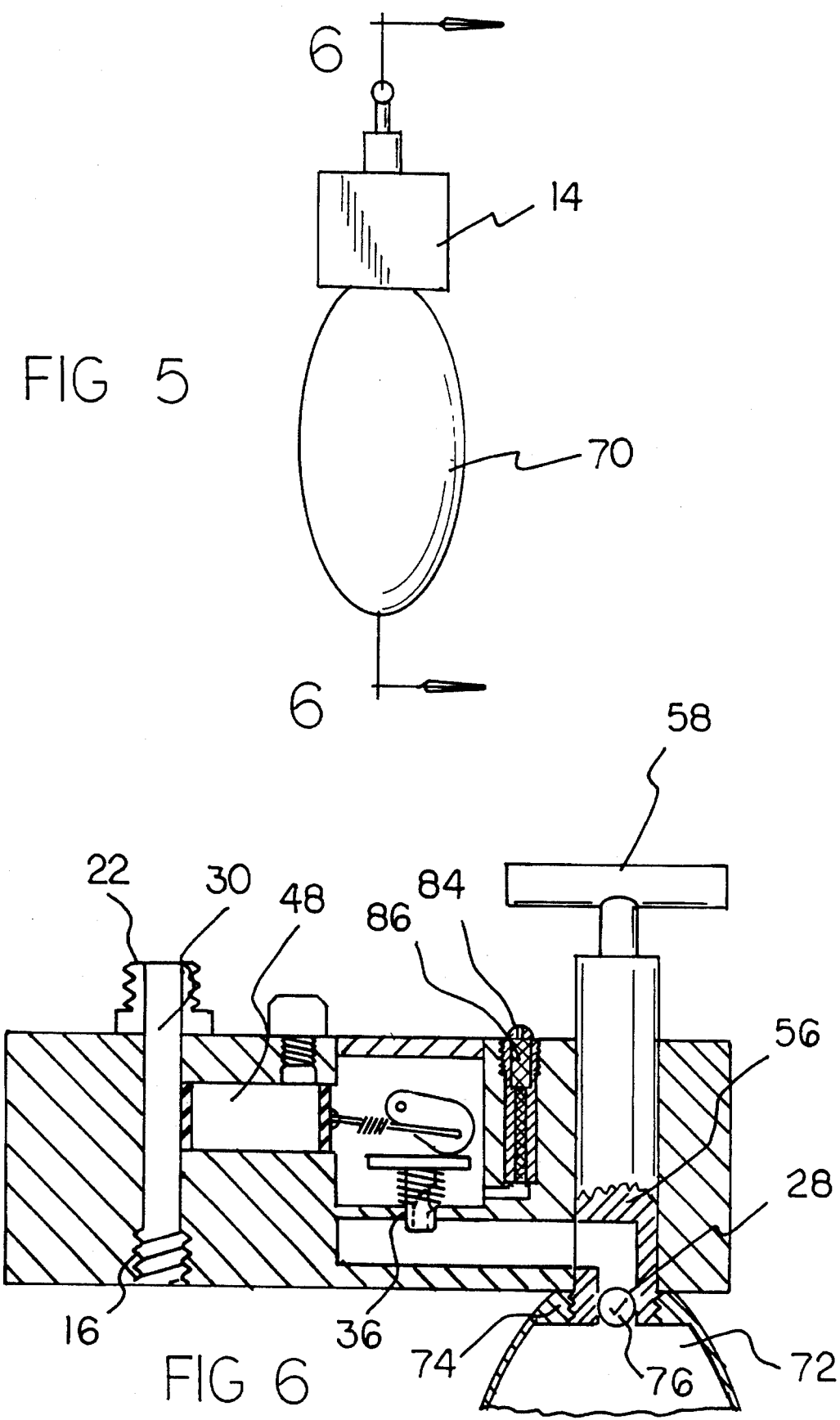

AMBIENT AIR COLLECTION DEVICE FOR USE WITH A SELF-CONTAINED BREATHING APPARATUS

BACKGROUND OF THE INVENTION

1. Field of the Invention

The present invention relates to an ambient air collection device for use with a self-contained breathing apparatus and more particularly pertains to collecting ambient air for subsequent analysis with an ambient air collection device for use with a self-contained breathing apparatus.

2. Description of the Prior Art

The use of ambient air collection mechanisms is known in the prior art. More specifically, ambient air collection mechanisms heretofore devised and utilized for the purpose of collecting ambient air for subsequent analysis are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,030,492 to Simbruner discloses a device for supporting human breathing and artificial respiration. U.S. Pat. No. 5,083,560 to Tillery, Jr. discloses a respiration monitor. U.S. Pat. No. 5,157,378 to Stumberg et al. discloses an integrated fire fighter safety monitoring and alarm system. U.S. Pat. No. 5,163,422 to Burgess discloses a breathing apparatus for providing a source of breathable air in a burning structure. U.S. Pat. No. 5,265,592 to Beaussant discloses individual protective breathing equipment.

While these devices fulfill their respective, particular objective and requirements, the aforementioned patents do not describe an ambient air collection device for use with a self-contained breathing apparatus that allows air samples to be collected for subsequent analysis.

In this respect, the ambient air collection device for use with a self-contained breathing apparatus according to the present invention substantially departs from the conventional concepts and designs of the prior art, and in doing so provides an apparatus primarily developed for the purpose of collecting ambient air for subsequent analysis.

Therefore, it can be appreciated that there exists a continuing need for new and improved ambient air collection device for use with a self-contained breathing apparatus which can be used for collecting ambient air for subsequent analysis. In this regard, the present invention substantially fulfills this need.

SUMMARY OF THE INVENTION

In the view of the foregoing disadvantages inherent in the known types of ambient air collection mechanisms now present in the prior art, the present invention provides an improved ambient air collection device for use with a self-contained breathing apparatus. As such, the general purpose of the present invention, which will be described subsequently in greater detail, is to provide a new and improved ambient air collection device for use with a self-contained breathing apparatus and method which has all the advantages of the prior art and none of the disadvantages.

To attain this, the present invention essentially comprises, in combination, a primary induction valve. The primary induction valve includes a rigid body, a threaded air inlet disposed on the body and adapted to be coupled to a pressure reducing assembly of a self-contained breathing apparatus for receiving a flow of breathable air therefrom, a threaded air outlet extended from the body and adapted to be coupled to an intake hose of a face mask of the self-contained breathing apparatus for delivering the flow of breathable air thereto, a threaded ambient air output port formed on the body, a first channel formed within the body and extended between the air inlet and air outlet for directing the flow of breathable air therebetween, an actuation chamber formed within the body and having an input port and an output port, a second channel formed within the body and extended from the first channel to the input port of the actuation chamber, a first diaphragm extended across the second channel at a location adjacent to the first channel, a second diaphragm extended across the input port of the actuation chamber with the diaphragms defining a gas chamber therebetween for holding gas, a pressure check valve threadedly coupled to the body and extended to the gas chamber for filling the gas chamber with gas and releasing gas contained therein, nitrogen gas disposed through the pressure check valve and into the gas chamber, an ambient air intake valve coupled to the body and extended to the actuation chamber for allowing flow of ambient air external to the body to the actuation chamber, a third channel formed within the body and extended from the output port of the actuation chamber to the ambient air output port for allowing delivery of ambient air within the actuation chamber to the ambient air output port, a spring-loaded pressure differential switch positioned within the output port of the actuation chamber and with the pressure differential switch having a biased orientation for allowing transfer of ambient air within the actuation chamber to the third channel and an unbiased orientation for preventing such transfer, an outlet valve coupled within the ambient air output port and having a handle extended from the body with the handle positionable in one orientation for allowing transfer of ambient air from within the third channel through the ambient air output port and with the handle positionable in another orientation for preventing such transfer, a cam positioned within the actuation chamber and abutted against the differential pressure switch, and a spring-loaded cam control rod extended between the second diaphragm and cam and with the diaphragms and cam control rod and cam positionable for urging the pressure differential switch to the biased orientation when breathable air flows through the first channel and further positionable for urging the pressure differential switch to the unbiased orientation when no breathable air flows through the first channel.

An elongated vacuum test cylinder is included for collecting ambient air. The vacuum test cylinder has a hollow vacuum pressurized interior, a threaded open end for allowing access to the interior, and a one-way check valve secured within the open end and with the open end threadedly coupled to the ambient air output port in one orientation such that the check valve is secured to the outlet valve of the primary induction valve for allowing transfer of ambient air to the interior of the vacuum test cylinder and with the open end decoupled from the ambient air output port in another orientation such that the check valve prevents escape of ambient air within the interior of the vacuum test cylinder.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved ambient air collection device for use with a self-contained breathing apparatus which has all the advantages of the prior art ambient air collection mechanisms and none of the disadvantages.

It is another object of the present invention to provide a new and improved ambient air collection device for use with a self-contained breathing apparatus which may be easily and efficiently manufactured and marketed.

It is a further object of the present invention to provide a new and improved ambient air collection device for use with a self-contained breathing apparatus which is of durable and reliable construction.

An even further object of the present invention is to provide a new and improved ambient air collection device for use with a self-contained breathing apparatus which is susceptible of a low cost of manufacture with regard to both materials and labor, and which accordingly is then susceptible of low prices of sale to the consuming public, thereby making such an ambient air collection device for use with a self-contained breathing apparatus economically available to the buying public.

Still yet another object of the present invention is to provide a new and improved ambient air collection device for use with a self-contained breathing apparatus which provides in the apparatuses and methods of the prior art some of the advantages thereof, while simultaneously overcoming some of the disadvantages normally associated therewith.

Even still another object of the present invention is to provide a new and improved ambient air collection device for use with a self-contained breathing apparatus for collecting ambient air for subsequent analysis.

Lastly, it is an object of the present invention to provide a new and improved ambient air collection device for use with a self-contained breathing apparatus comprising a primary induction valve having a body, an air inlet, an air outlet, an ambient air output port, a channel formed within the body and extended between the air inlet and air outlet for transferring breathable air therebetween, an actuation chamber formed within the body and having an input port coupled to the channel and an output port coupled to the ambient air output port, an ambient air intake valve coupled to the actuation chamber for delivering ambient air thereto, switch means positioned within the input port and output port of the actuation chamber with the switch means having a biased orientation for allowing transfer of ambient air within the actuation chamber to the ambient air output port based upon detection of a flow of breathable air through the channel and an unbiased orientation for preventing such transfer when no flow is detected; and a removable hollow vacuum pressurized vacuum test cylinder coupled to the ambient air output port for collecting ambient air therefrom.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a view of the preferred embodiment constructed in accordance with the principles of the present invention secured between a face mask regulator and a pressure reducing assembly and air tank of a self-contained breathing apparatus.

FIG. 4 is an enlarged view of the present invention decoupled from a self-contained breathing apparatus.

FIG. 5 is a side-elevational view of the present invention taken along the line 5—5 of FIG. 4.

FIG. 6 is a cross-sectional view of the present invention taken along the line 6—6 of FIG. 5.

The same reference numerals refer to the same parts through the various Figures.

DESCRIPTION OF THE PREFERRED EMBODIMENT

Figure 1:
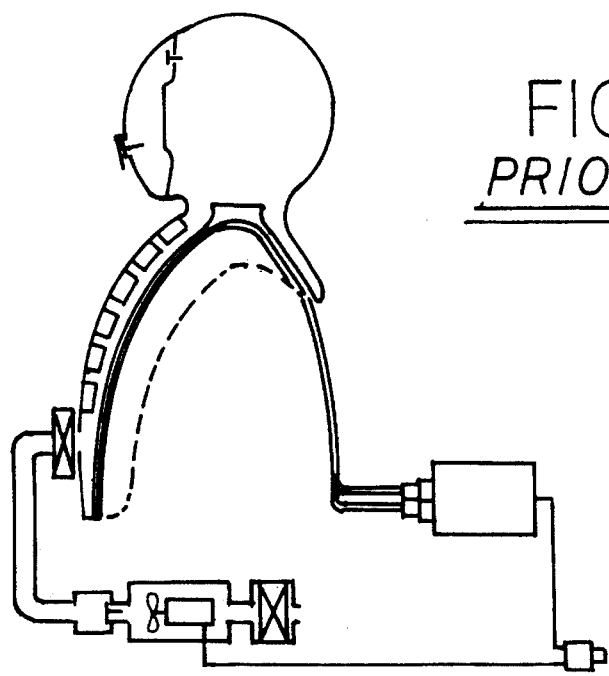
FIG. 1 is a cross-sectional view of a prior art individual protective breathing apparatus.
Figure 2:
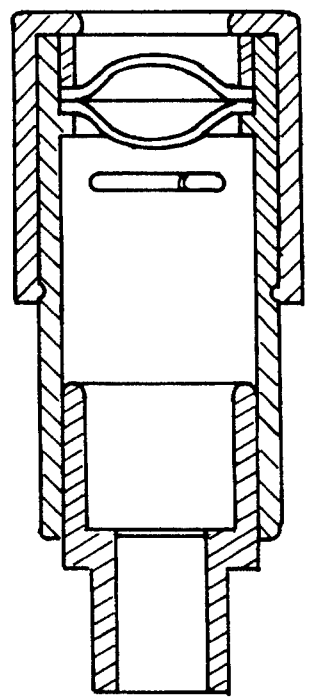
FIG. 2 is a cross-sectional view of a prior art respiration monitor.
Figure 7:
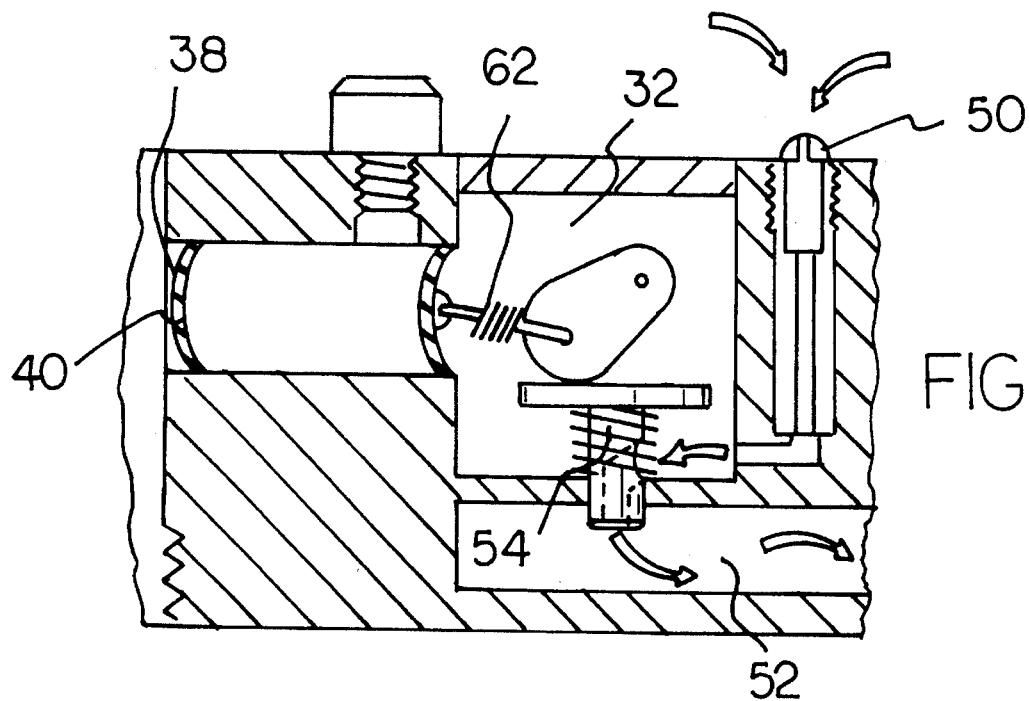
FIG. 7 is an enlarged cross-sectional view of the primary induction valve in an actuated state for allowing flow of ambient air therethrough for subsequent collection in the vacuum test cylinder.
Figure 8:
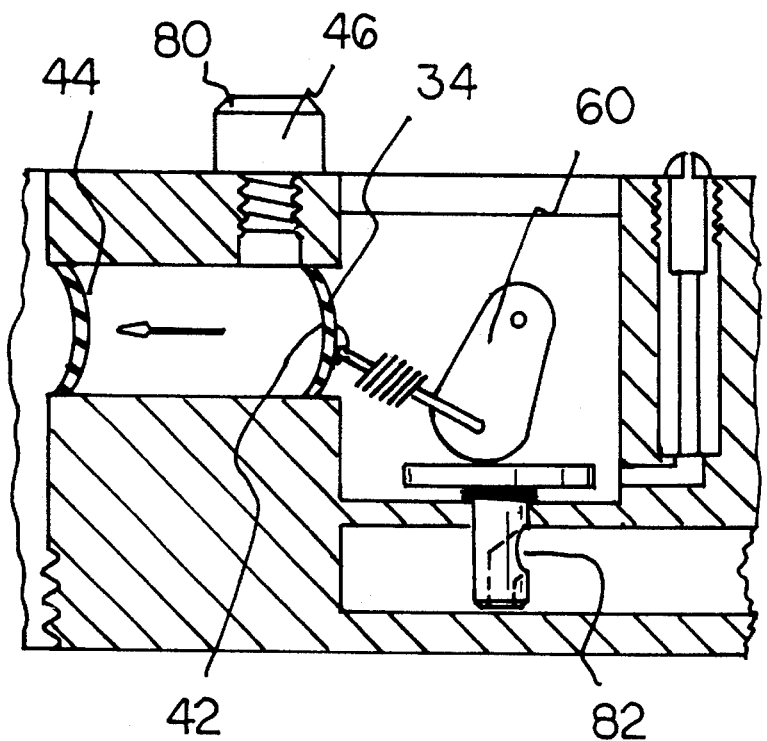
FIG. 8 is yet another cross-sectional view of the primary induction valve in a de-actuated state for preventing flow of ambient air therethrough.

With reference now to the drawings, and in particular, to FIG. 1 thereof, the preferred embodiment of the new and improved ambient air collection device for use with a self-contained breathing apparatus embodying the principles and concepts of the present invention and generally designated by the reference number 10 will be described.

Specifically, the present invention essentially includes two major components. The major components are the primary induction valve and the vacuum test cylinder. These components are interrelated to provide the intended function.

More specifically, it will be noted in the various Figures that the first major component is the primary induction valve 12. The primary induction valve has a rigid body formed of metal, plastic, or other suitable material. A threaded air inlet 16 is disposed on the body. The threaded air inlet is adapted to be coupled to a pressure reducing assembly 18 of a self-contained breathing apparatus. The pressure reducing assembly is also coupled to an air tank 20 of the self-contained breathing apparatus. The air inlet is used for receiving a flow of breathable air from the air tank 20. The primary induction valve also includes a threaded air outlet 22. The air outlet is extended from the body. The air outlet is adapted to be coupled to an intake hose 24 of a face mask 26 of the self-contained breathing apparatus. The air outlet delivers breathable air to the face mask for use. The primary induction valve includes a threaded ambient air outlet port 28. The ambient air outlet port is formed on the body. A first channel 30 is formed within the body and extended between the air inlet and air outlet. The first channel is used for directing the flow of breathable air from the air inlet to the air outlet. The primary induction valve includes an actuation chamber 32 formed within the body. The actuation chamber has an input port 34 and an output port 36. A second channel 38 is formed within the body and extended from the first channel to the input port of the actuation chamber. A first diaphragm 40 formed of a flexible material is extended across the second channel at a location adjacent to the coupling of the second channel with the first channel. A second diaphragm 42 formed of a flexible material is extended across the input port of the actuation chamber. The diaphragms thus define a gas chamber 44 therebetween for holding gas therein. The primary induction valve includes a pressure check valve 46 threadedly coupled to the body and extended to the gas chamber. The pressure check valve is used for filling the gas chamber with gas and releasing gas contained therein. Nitrogen gas 48 or other generally inert gas is disposed through the pressure check valve and into the gas chamber. The primary induction valve includes an ambient air intake valve 50. The ambient air intake valve is coupled to the body and extended to the actuation chamber. The ambient air intake valve allows flow of ambient air external to the body to the actuation chamber. A third channel 52 is formed within the body and extended from the output port of the actuation chamber to the ambient air output port. The third channel thus allows delivery of ambient air within the actuation chamber to the ambient air output port. The primary induction valve includes a spring-loaded pressure differential switch 54. The pressure differential switch is positioned within the output port of the actuation chamber. The pressure differential switch has a biased orientation for allowing transfer of ambient air within the actuation chamber to the third channel. The pressure differential switch also has an unbiased orientation for preventing such transfer. The primary induction valve includes an outlet valve 56. The outlet valve is coupled within the ambient air output port. The outlet valve has a handle 58 extended from the body. This handle is positionable in one orientation for allowing transfer of ambient air from within the third channel through the ambient air output port. The handle is also positionable in another orientation for preventing the transfer of ambient air from within the third channel through the ambient air output port. A cam 60 is positioned within the actuation chamber and abutted against the differential pressure switch. A spring-loaded cam control rod 62 is extended between the second diaphragm and cam. The first and second diaphragms, cam control rod, and cam are positionable for urging the pressure differential switch to the biased orientation for collecting ambient air when breathable air flows through the first channel. The second diaphragm, cam control rod, and cam are also positionable for urging the pressure differential switch to the unbiased orientation for preventing collection of ambient air when no breathable air flows through the first channel.

The second major component is the vacuum test cylinder 70. The vacuum test cylinder is elongated and rigid in structure. It is formed of plastic, metal, or other similar material. The vacuum test cylinder is used for collecting ambient air. The vacuum test cylinder has a hollow vacuum pressurized interior 72 and a threaded open end 74 for allowing access to the interior. A one-way check valve 76 is secured within the open end. The open end is then threadedly coupled to the ambient air output port of the primary induction valve. In this orientation, the check valve is secured to the outlet valve 56 of the primary induction valve for allowing transfer of ambient air to the interior of the vacuum test cylinder. The open end of the vacuum test cylinder is also decouplable from the ambient air output port in another orientation such that the check valve prevents escape of ambient air within the interior of the vacuum test cylinder. Thus, the vacuum test cylinder may be separated from the primary induction valve and transported to a remote location for analyzing the ambient air contained therein.

Construction of homes and commercial buildings are fabricated from a myriad of materials. All or most of these materials are harmless to living things when used in the correct fashion. When these materials are exposed to a catalyst or to conditions outside of the normal original operating environments, the materials change to, or emit, hazardous chemicals. A specific catalyst in point is heat. A building that is aflame changes these materials to a hazardous and toxic form. With numerous materials on fire simultaneously, the air can quickly become infiltrated with an large number of combinations of hazardous elements. Exposure to these hazardous chemicals to the skin, or inhalation to the respiratory system can lead to a chain of catastrophic medical events.

The type of personnel that are exposed to this on a daily basis are fire fighters. Their job requires them to work in extremely dangerous environments. To date, fire fighters enter environments that are filled with products of combustion (smoke). When heated to extremes the common materials mentioned above will readily release by-products containing toxic chemicals (that are carried in the smoke). Many of these by-products are carcinogenic. Fire fighters' protective gear offers limited skin protection.

Fire fighters use a standard self-contained breathing apparatus (SCBA) when they enter smoke filled structures. This SCBA offers protection to a fire fighter's face and lungs but does nothing to provide protection to exposed skin surfaces. These toxins can be absorbed by (or adhere to the external surfaces of) fire fighters' equipment, thus increasing exposure to toxins by incidental contact.

The purpose of the present invention is to accurately record an individual's occupational exposure to potential toxins in ambient air. In the event of a future medical health problem of an individual, this record will provide medical personnel with the exact content of material/toxins to which the individual was exposed. The present invention is an assessment tool used to evaluate risk management procedures service wide. The present invention is used with a SCBA. The SCBA consists of a high-pressure air tank 20, a pressure reducing assembly 18, and a face mask regulator 26 with accompanying interface hose 24 and fittings. The SCBA has an air tank that is carried on the fire fighter's back. The air within the tank is held at a high pressure (about 4500 PSI) to allow a long usage time. The pressure within the tank is too high for one to effectively inhale, so a pressure reducing assembly is required. The pressure reducing assembly interfaces between the air tank and the face mask hose assembly of the SCBA and reduces the air pressure from about 4500 to about 185 PSI. The air pressure at the face mask is now at a pressure that can be effectively and safely inhaled. The face mask provides a sealed fit to the fire fighter's face. An integral part of the face mask is a regulator that allows the fire fighter to breath as normal.

The present invention consists of a primary induction valve and a vacuum test cylinder. The primary induction valve interfaces between the pressure reducing assembly and the face mask hose assembly of the SCBA. The present invention does not interfere with the normal operation of the SCBA system and is a fail-safe design. The vacuum test cylinder is a removable, reusable, and hollow cylinder. The vacuum test cylinder is vacuum pressurized and threadedly coupled and sealed with the primary induction valve with a complementary O-ring. The primary induction valve includes a cylindrical gas chamber that has a sealed diaphragm at both ends. The gas chamber of the present invention is filled with nitrogen gas, and this gas acts as a controlled medium. As the fire fighter breathes, the regulator opens and allows air to flow (pressure change) from the pressure reducing assembly to the regulator of the face mask. This air movement pulls the first diaphragm in towards the air flow. As the diaphragm is pulled in it slightly alters the nitrogen filled medium thereby causing the second diaphragm to bend inward towards the breathable air flow. The second diaphragm controls a spring-tension cam that momentarily opens the pressure differential switch. The vacuum test cylinder is vacuum pressurized and the negative pressure draws in a small sample of ambient air. This completes one cycle of operation of the present invention. The vacuum test cylinder contains enough vacuum pressure to draw in ambient air samples for a period of about 30 minutes.

The primary induction valve utilizes nitrogen gas because it is inert, is readily available, is non-flammable, and has excellent pressurization properties. Since the primary induction valve interfaces with the fire fighter's breathable air source and since the present invention is designed as a fail safe system, the SCBA operates as normal if the present invention fails.

An indicator 80 can be incorporated into pressure check valve the primary induction valve of the present invention to provide a confidence check for fire fighters. This indicator clearly shows green when the primary induction valve is fully operational and red in the event of a failure. The indicator changes color when the nitrogen gas in the gas chamber leaks out due to diaphragm failure or crack in the body. The indicator alerts the fire fighter and/or maintenance personnel. The one-way check valve located at the ambient air output port insures that a sample of ambient air does not evacuate when the vacuum test cylinder pressure equals the ambient atmospheric pressure.

As previously stated the vacuum test cylinder is threaded into the ambient air output port of the primary induction valve. After the vacuum test cylinder is installed, the handle on the top of it must be rotated ½ of a turn to the "ON" position. A detent in the handle prohibits it from being accidently turned off. Positioning the handle to the "ON" position rotates a hollow shaft upward. This allows an entrance hole 82 in the shaft to be exposed and enter the negative pressure side of the pressure differential switch. The present invention is now ready for use. After usage, the vacuum test cylinder tank has to be removed and sent to a qualified laboratory for analysis. The one-way check valve insures that the sampled air will not be released if the tank is removed with the handle in the "ON" position. This is yet another fail safe feature that eliminates accidental loss of the collected sample, and possible tampering.

The pressure differential switch is spring-loaded and opens momentarily with each breath that the fire fighter takes. As the fire fighter takes a breath, the secondary diaphragm of the primary induction valve is pulled outward away from the actuation chamber. As the diaphragm is pulled outward it applies pressure on the spring-loaded cam control rod. As the rod moves it rotates the cam and allows the spring-loaded pressure differential switch to rise. The pressure differential switch has a shaft with an entrance hole on its side and is hollow with the bottom end open. When the entrance hole is exposed to ambient air, the vacuum test cylinder vacuum pressure draws in a sample. The ambient air intake valve is covered by protective screen 84 and under the screen is a paper filter element 86 that restricts large particles from blocking the valve in the open position.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. An ambient air collection device for use with a self-contained breathing apparatus for collecting ambient air for subsequent analysis comprising, in combination:

a primary induction valve having a rigid body, a threaded air inlet disposed on the body and adapted to be coupled to a pressure reducing assembly of a self-contained breathing apparatus for receiving a flow of breathable air therefrom, a threaded air outlet extended from the body and adapted to be coupled to an intake hose of a face mask of the self-contained breathing apparatus for delivering the flow of breathable air thereto, a threaded ambient air output port formed on the body, a first channel formed within the body and extended between the air inlet and air outlet for directing the flow of breathable air therebetween, an actuation chamber formed within the body and having an input port and an output port, a second channel formed within the body and extended from the first channel to the input port of the actuation chamber, a first diaphragm extended across the second channel at a location adjacent to the first channel, a second diaphragm extended across the input port of the actuation chamber with the diaphragms defining a gas chamber therebetween for holding gas, a pressure check valve threadedly coupled to the body and extended to the gas chamber for filling the gas chamber with gas and releasing gas contained therein, nitrogen gas disposed through the pressure check valve and into the gas chamber, an ambient air intake valve coupled to the body and extended to the actuation chamber for allowing flow of ambient air external to the body to the actuation chamber, a third channel formed within the body and extended from the output port of the actuation chamber to the ambient air output port for allowing delivery of ambient air within the actuation chamber to the ambient air output port, a spring-loaded pressure differential switch positioned within the output port of the actuation chamber and with the pressure differential switch having a biased orientation for allowing transfer of ambient air within the actuation chamber to the third channel and an unbiased orientation for preventing such transfer, an outlet valve coupled within the ambient air output port and having a handle extended from the body with the handle positionable in one orientation for allowing transfer of ambient air from within the third channel through the ambient air output port and with the handle positionable in another orientation for preventing such transfer, a cam positioned within the actuation chamber and abutted against the differential pressure switch, and a spring-loaded cam control rod extended between the second diaphragm and cam and with the diaphragms and cam control rod and cam positionable for urging the pressure differential switch to the biased orientation when breathable air flows through the first channel and further positionable for urging the pressure differential switch to the unbiased orientation when no breathable air flows through the first channel; and an elongated vacuum test cylinder for collecting ambient air having a hollow vacuum pressurized interior, a threaded open end for allowing access to the interior, and a one-way check valve secured within the open end and with the open end threadedly coupled to the ambient air output port in one orientation such that the check valve is secured to the outlet valve of the primary induction valve for allowing transfer of ambient air to the interior of the vacuum test cylinder and with the open end decoupled from the ambient air output port in another orientation such that the check valve prevents escape of ambient air within the interior of the vacuum test cylinder.

2. An ambient air collection device comprising:

a primary induction valve having a body, an air inlet, an air outlet, an ambient air output port, a channel formed within the body and extended between the air inlet and air outlet for transferring breathable air therebetween, an actuation chamber formed within the body and having an input port coupled to the channel and an output port coupled to the ambient air output port, an ambient air intake valve coupled to the actuation chamber for delivering ambient air thereto, switch means positioned within the input port and output port of the actuation chamber with the switch means having a biased orientation for allowing transfer of ambient air within the actuation chamber to the ambient air output port based upon detection of a flow of breathable air through the channel and an unbiased orientation for preventing such transfer when no flow is detected; and a removable hollow vacuum pressurized vacuum test cylinder coupled to the ambient air output port for collecting ambient air therefrom.

3. The ambient air collection device as set forth in claim 2 wherein the switch means comprises:

a first diaphragm extended across the input port of the actuation chamber;

a second diaphragm extended across the input port of the actuation chamber at a location offset from the first diaphragm such that the diaphragms define a gas chamber therebetween for holding gas;

a pressure check valve coupled to the body and extended to the gas chamber for filling the gas chamber with gas and releasing gas contained therein;

a generally inert gas disposed through the pressure check valve and into the gas chamber;

a spring-loaded pressure differential switch positioned within the output port of the actuation chamber with the pressure differential switch having a biased orientation for allowing transfer of ambient air within the actuation chamber to the third channel and an unbiased orientation for preventing such transfer;

a cam positioned within the actuation chamber and abutted against the differential pressure switch; and a spring-loaded cam control rod extended between the second diaphragm and cam and with the second diaphragm and cam control rod and cam positionable for urging the pressure differential switch to the biased orientation when breathable air flows through the channel and further positionable for urging the pressure differential switch to the unbiased orientation when no breathable air flows through the channel.

4. The ambient air collection device as set forth in claim 2 further including an outlet valve coupled within the ambient air output port and having a handle extended from the body with the handle positionable in one orientation for allowing transfer of ambient air through the ambient air output port and with the handle positionable in another orientation for preventing such transfer.

5. The ambient air collection device as set forth in claim 2 wherein the vacuum test cylinder includes a one-way check valve secured thereto for preventing ambient air from escaping once it has been collected.

* * * * *